(12) United States Patent
Palmaz et al.

(10) Patent No.: US 11,559,668 B2
(45) Date of Patent: Jan. 24, 2023

(54) DRUG-ELUTION CONTROL SLEEVE FOR DRUG-ELUTING BALLOON AND METHOD

(71) Applicant: Vactronix Scientific, LLC, Fremont, CA (US)

(72) Inventors: Christian G. Palmaz, Fremont, CA (US); Julio C. Palmaz, Napa, CA (US); Scott P. Carpenter, Fremont, CA (US)

(73) Assignee: Vactronix Scientific, LLC., San Antonio, TX (US)

( * ) Notice: Subject to any disclaimer, the term of this patent is extended or adjusted under 35 U.S.C. 154(b) by 165 days.

(21) Appl. No.: 16/796,901

(22) Filed: Feb. 20, 2020

(65) Prior Publication Data

US 2020/0269020 A1   Aug. 27, 2020

Related U.S. Application Data

(60) Provisional application No. 62/808,662, filed on Feb. 21, 2019.

(51) Int. Cl.
*A61M 25/10* (2013.01)

(52) U.S. Cl.
CPC ........ *A61M 25/10* (2013.01); *A61M 25/1027* (2013.01); *A61M 2025/105* (2013.01);
(Continued)

(58) Field of Classification Search
CPC ............ A61M 25/10; A61M 2025/108; A61M 2025/1086; A61M 2025/109; A61F 2/07
See application file for complete search history.

(56) References Cited

U.S. PATENT DOCUMENTS

| 8,388,573 B1 | 3/2013 | Cox .................... 604/103.01 |
| 2002/0013619 A1* | 1/2002 | Shanley ................ A61F 2/915 623/1.15 |

(Continued)

FOREIGN PATENT DOCUMENTS

| CN | 206325106 | 7/2017 | ............ A61M 25/10 |
| EP | 1222941 | 5/2006 | ............ A61M 29/00 |

(Continued)

OTHER PUBLICATIONS

International Search Report and Written Opinion issued in corresponding foreign application, PCT/US2020/019226, pp. 1-13 (dated Jul. 14, 2020).

*Primary Examiner* — Theodore J Stigell
*Assistant Examiner* — Rachel T. Smith
(74) *Attorney, Agent, or Firm* — David G. Rosenbaum; Rosenbaum IP, P.C.

(57) ABSTRACT

An apparatus, assembly and method for controlling release of a drug from a drug-eluting balloon during delivery of a drug-eluting balloon to a situs within a body. More particularly, the present invention relates to a diametrically expandable sleeve having a first non-diametrically unexpanded state in which drug retained on or in a drug-eluting balloon is protected from release by a sleeve and a second diametrically expanded state in which drug retained on or in the drug-eluting balloon is exposed for focal release in the body by diametric expansion of the sleeve, exposing openings in the sleeve during diametric expansion and closing the openings in the sleeve when the sleeve is in its diametrically unexpanded state.

23 Claims, 11 Drawing Sheets

(52) U.S. Cl.
CPC .............. *A61M 2025/1079* (2013.01); *A61M 2205/0266* (2013.01)

(56) References Cited

U.S. PATENT DOCUMENTS

| | | | |
|---|---|---|---|
| 2005/0216047 A1* | 9/2005 | Kumoyama | A61M 25/104 606/191 |
| 2014/0371786 A1 | 12/2014 | Kornblau et al. | |
| 2015/0190618 A1* | 7/2015 | Kantor | B32B 37/142 604/509 |
| 2020/0214825 A1* | 7/2020 | Gassler | A61F 2/92 |

FOREIGN PATENT DOCUMENTS

| | | | | |
|---|---|---|---|---|
| WO | WO 1996-08286 | | 3/1996 | ............ A61M 25/00 |
| WO | WO-9608286 A1 * | | 3/1996 | ............... A61B 8/12 |
| WO | WO 1998-039056 | | 9/1998 | ............ A61M 29/02 |
| WO | WO 2003-015840 | | 2/2003 | ............ A61M 29/00 |
| WO | WO 2016-164420 | | 10/2016 | ............. A61F 2/958 |
| WO | WO 2017-087507 | | 5/2017 | ............. A61F 2/958 |

* cited by examiner

DRUG-ELUTION CONTROL SLEEVE FOR DRUG-ELUTING BALLOON AND METHOD

CROSS-REFERENCE TO RELATED APPLICATIONS

The present application claims priority to commonly assigned U.S. provisional application Ser. No. 62/808,662 filed Feb. 21, 2019, herein incorporated by reference in its entirety.

BACKGROUND OF THE INVENTION

The present inventions relates generally to a device for controlling release of a drug from a drug-eluting balloon during delivery of the drug-eluting balloon to a situs within a body. More particularly, the present invention relates to a diametrically expandable sleeve having a first non-diametrically unexpanded state in which drug retained on or in a drug-eluting balloon is protected from release and a second diametrically expanded state in which drug retained on or in the drug-eluting balloon is exposed for focused localized release in the body.

Drug-eluting balloon catheters are frequently used in treating diseased vasculature, particularly the coronary and peripheral vasculature. Drug-eluting balloon catheters also have potential application in other anatomic passageways, including, without limitation, coronary valves, atrial or ventricular chambers of the heart, with neuro-interventional pathologies, within the perivascular spaces in the brain, in the subarachnoid or subdural spaces or within the spinal canal.

Localized pathologies, such as vascular disease, often respond more favorably to focal treatment at the localized site of the pathology rather than systemic treatment. Thus, it is desirable to provide a drug-eluting balloon device that safeguards against premature release of drug during delivery or deployment of the drug-eluting balloon device.

A primary difficulty with current drug-eluting balloons is that the drug is subjected to washout by the blood flow either during navigating the tortuous passageways to a delivery site or at a delivery site. Drug washout reduces the amount of drug present for therapeutic delivery at the desired situs within the body as a result of loss of drug in the blood flow. Washout also creates the risk of broader systemic drug effects. Thus, it is highly desirable to provide an improved drug eluting balloon delivery system and method that safeguards against drug washout and permits focused localized delivery to the desired situs within the body.

Current drug-eluting balloons typically fall in two general classes. First are porous balloons That deliver a drug infused through a catheter into a space within the balloon and through the porous wall of the balloon. Second are balloons having a smooth outer surface with a coating layer, such as a hydrogel or other polymer, capable of retaining the drug and allowing the drug to elute from the coating layer.

Several attempts have been made to protect the outer surface of a drug-eluting balloon during delivery and deployment with retractable sheaths or cages configured to act as a spacer between the balloon surface and the vascular tissue. These devices, however, do not appear to solve the technical problems of increased device profile, longitudinal flexibility for trackability while navigating tortuous vascular passageways, and restricting the premature release of drug from the balloon. Moreover, none of the current devices employ an elution sleeve which is configured to have a first substantially two-dimensional smooth delivery surface profile in which openings in the elution sleeve have dimensions configured to prevent drug from eluting through the openings when the balloon and sleeve are in a first diametrically unexpanded state during delivery of the balloon to a situs within the body and a second substantially three-dimensional surface profile when the balloon and sleeve are in a second diametrically expanded state at the situs within the body. The substantially two-dimensional surface profile is characterized by substantially all of the elongate members having outer surfaces laying substantially co-planar with each other when the sleeve is in an unexpanded diametric state. When the sleeve is in a diametrically expanded state, the substantially three-dimensional surface profile is characterized by having at least some of the elongate members having at least a portion of their outer surfaces projecting out of plane relative to other portions of the elongate members. The out of plane position of the elongate members may assume a wide number of geometries that impart a surface texture to the sleeve. Such surface textures may include the elongate members assuming a sinusoidal, undulating or saw-tooth shape in the Z-axis of the sleeve projecting radially outward from the central longitudinal axis of the catheter.

In the three-dimensional surface profile, the elongate members of the sleeve will have deformed and at least a portion of the elongate members will have angularly rotated about their axes such that a lateral surface of an elongate member will be positioned to project outward from the sleeve. In this outwardly projecting position, the Z-axis thickness of an elongate member is outwardly exposed and, when the sleeve is expanded against a diseased surface in the body, such as vascular plaque, the elongate member acts as a cutting surface to penetrate into the diseased tissue. This penetration of the elongate member into the diseased tissue is quite small, typically less than the width of an elongate member, yet the penetration provides a focused pathway into the diseased tissue for penetration of a drug released from an underlying drug-eluting balloon.

SUMMARY OF THE INVENTION

It is an object of the present invention to provide a diametrically expandable sleeve for covering a drug-eluting balloon during handling, delivery and deployment that substantially encloses the drug-eluting balloon and prevent drug on or in the balloon from releasing from the balloon when the balloon is in its diametrically unexpanded state and which opens upon diametric expansion of the sleeve to allow focused drug release through the sleeve from the balloon.

It is a further object of the present invention to provide a drug-elution sleeve which is capable of pseudoelastic deformation under the influence of balloon inflation pressures.

It is another objective of the present invention to provide a drug-elution sleeve made of a shape memory or super-elastic metal, pseudometal or polymer having a thickness between greater than or equal to 0.1 µm and less than or equal to 75 µm.

It is yet another objective of the present invention to provide a drug-elution sleeve in which a pattern of slits that define elongate strut members of the drug-elution sleeve, with the pattern of slits imparting both longitudinal and circumferential compliance to the drug-elution sleeve as well as allow for geometric deformation of the slits during diametric expansion of the drug-elution sleeve.

It is still another objective of the present invention to provide a drug-elution sleeve in which a plurality of slits pass through a thickness of the sleeve and have a width less than or equal to 25 µm when the sleeve is in its diametrically unexpanded state.

It is yet still another objective of the present invention to provide a drug-elution sleeve in which a plurality of slits passing through the thickness of the sleeve each have a length greater than 1 mm.

It is another objective of the present invention to provide a drug-elution sleeve in which the plurality of slits passing through the thickness of the sleeve have an aspect ratio of length to width greater than or equal to 1:500.

It is still another objective of the present invention to provide a drug-elution sleeve in which the plurality of slits have an aspect ratio of less than or equal to 1:120.

It is still another objective of the present invention to provide a drug-elution sleeve having a proximal and/or distal attachment region configured to attach the drug-elution sleeve to a catheter and surrounding a drug-eluting balloon.

DETAILED DESCRIPTION OF THE PREFERRED EMBODIMENTS

The present invention will be described with reference to the accompanying Figures, in which like elements are identified by like reference numerals. While the present invention will be described with reference to certain preferred embodiments, those of ordinary skill in the art will understand and appreciate that variations in materials, structure, material properties, and tolerances may be made without departing from the scope of the invention, which is limited only by the claims appended hereto and their range of equivalents.

For purposes of clarity, the following terms used in this patent application will have the following meanings:

"Substantially" is intended to mean a quantity, property, or value that is present to a great or significant extent and less than and including totally.

"About" is intended to mean a quantity, property, or value that is present at +10%.

"Pseudometallic" or "Pseudometal" is intended to mean a biocompatible material which exhibits biological response and material characteristics substantially the same as biocompatible metals. Examples of pseudometallic materials may include composite materials, ceramics, quartz, and borosilicate. Composite materials are composed of a matrix material reinforced with any of a variety of fibers made from ceramics, metals, or polymers. The reinforcing fibers are the primary load carriers of the material, with the matrix component transferring the load from fiber to fiber. Reinforcement of the matrix material may be achieved in a variety of ways. Fibers may be either continuous or discontinuous. Reinforcement may also be in the form of particles. Examples of composite materials include those made of carbon fibers, boron fibers, boron carbide fibers, carbon and graphite fibers, silicon carbide fibers, steel fibers, tungsten fibers, graphite/copper fibers, titanium and silicon carbide/titanium fibers.

"Pseudoelastic deformation" is intended to mean a deformation caused by an applied load that is completely recoverable upon removal of the load and the limit of which is characterized by being significantly larger than the elastic limit of a traditional metal (e.g., 8% strain in the case of nitinol). This phenomenon is caused by a load or stress induced solid-state phase change that is reversible upon removal of the load.

"Shape memory alloy" is intended to mean a binary, ternary, quaternary metal alloy that recover apparent permanent strains when raised above an Austenitic transformation temperature ($A_s$). Shape memory alloys have two stable phases, i.e., a high-temperature or austenite phase and a low-temperature or martensite phase.

"Superelastic" is intended to mean a property of a material characterized by having a reversible elastic response in response to an applied stress. Superelastic materials exhibit a phase transformation between the austenitic and martensitic phases as the applied stress is loaded or unloaded.

"Radiopaque" is intended to mean any material that obstructs passage of radiation and increases background contrast in X-rays or similar radiation images.

A stress-strain curve for a shape memory or superelastic material, such as austenitic nitinol, in which a sample is taken all the way to failure at a temperature above $A_f$ (finish of Austenitic transformation) can be separated into the following regions of the stress-strain curve: elastic deformation of austenite, pseudoelastic deformation of austenite to stress induced martensite, elastic deformation of the stress induced martensite, plastic deformation of the stress induced martensite and fracture. Removal of the load at any point before the onset of plastic deformation of the stress induced martensite will result in complete recovery of the deformation.

The sleeve of the present invention is preferably made of a shape memory or superelastic material, including metals, pseudometals and polymers. Particularly preferred materials are binary, ternary or quaternary nickel-titanium based metal alloys, such as nitinol. Shape memory and/or superelastic metal alloys may be binary, ternary, quaternary, quinary or n-ary, where n-is an integer of the base value metal alloys. While binary nickel-titanium alloys are well known in the art, other alloy additions of iron, copper, chromium, vanadium, niobium, bismuth, cobalt, tungsten, platinum, palladium, tantalum, zirconium, hafnium and/or gold may also be used. Certain radiopaque elements may, such as tungsten, bismuth, cobalt, or tantalum, may be employed, either as an alloying element or as a discrete layer in the sleeve, to increase the sleeve's radiopacity.

When a nitinol alloy is employed, it is typically in a thermally-induced martensitic state where the material is brought to a temperature below $M_f$ (finish of martensitic transformation) and subsequently kept below $A_s$ (onset of austenitic transformation). If the material is sufficient deformed (greater than 0.5% strain) while in its thermally-induced martensitic state and subsequently constrained at temperatures above $A_s$, it is still considered to be in its thermally-induced martensite state and not in a stress-induced martensite state. A stress-strain curve for martensitic nitinol in which a sample is taken all the way to failure at a temperature below $A_s$ can be separated into the following regions: elastic deformation of thermally induced martensite, pseudoplastic deformation of thermally induced martensite via detwinning, elastic deformation of the detwinned thermally induced martensite, plastic deformation of the detwinned thermally induced martensite and fracture. Removal of the load at any point before the onset of plastic deformation of the detwinned thermally induced martensite will result in complete recovery of the deformation when heated above $A_f$.

In accordance with its most general aspect, the present invention relates to a diametrically expandable sleeve concentrically coupled to an outer surface of a drug-eluting balloon. The sleeve is substantially tubular and has a plurality of slits passing through the sleeve walls that geometrically deform from a closed position when the drug-eluting balloon and sleeve are in an unexpanded diametric state to an open position when the drug-eluting balloon and sleeve are in a diametrically expanded state. When the sleeve is in a diametrically unexpanded state and the slits are in their closed position, the slits have an open area configure to restrict drug in or on the drug-eluting balloon from passing through the slits. When delivered to a situs within a body and placed in a desired location, the sleeve will be in apposition to biological tissue. As the balloon is inflated, such as by infusion of a pressurized fluid into the balloon, the sleeve will diametrically expand and the plurality of slits geometrically deform to their open position, the open areas of the slits expose the drug-eluting balloon beneath the sleeve. Once the exposed to the adjacent biological tissue, the drug carried on the drug-eluting balloon will elute through the open slits to the adjacent biological tissue. Upon deflation of the balloon, the sleeve will diametrically collapse on the balloon, with the plurality of slits closing and reassuming their substantially closed position on the balloon.

The sleeve also has land regions between the plurality of slits that geometrically deform as the sleeve and drug-eluting balloon are expanded from the diametrically unexpanded state to the diametrically expanded state. These land regions are typically elongate strut members having hinge regions at opposing ends of the elongate strut members. For purposes of this application, the land regions will also be referred to synonymously as elongate strut members. The hinge regions act as pivot points to distribute the strain associated with deformation of the land regions during diametric expansion and contraction of the sleeve. Each of the land regions has a width, length and thickness. As the land regions are defined between adjacent slits, the width of a land region is determined by the spacing of the slits. Land region widths may be between about 5 μm and about 50 μm, while lengths may be between 25 μm and 500 μm. Land region thickness will be equivalent to the thickness of the sleeve. The land regions will typically have generally quadrilateral transverse cross sections with a luminal surface that faces the lumen of the sleeve, and abluminal surface that faces away from the lumen of the sleeve and lateral surfaces that face each of the slits adjacent to and bounding the land region, all when the sleeve is in its unexpanded diameter. The plurality of land regions may each move in the X-Y plane of the sleeve and may also each move in the Z-axis of the sleeve by rotating about their individual axes. When each of the plurality of land regions rotate about their own axis, each land region assumes an twisted and arcuate configuration in which a lateral surface of each rotated land region projects outwardly above the X-Y plane of the sleeve. In this manner the twisted and arcuate portion that projects radially outwardly exposes a portion of the lateral surface of the land region, as opposed to the luminal or abluminal surface, to the biological tissue against which the sleeve and balloon are in apposition. The twisted and arcuate lateral surfaces of the land regions that project outwardly from the plane of the sleeve assist in penetrating or pressing into adjacent biological tissue, such as vascular tissue, which, in turn, aids in drug absorption into the biological tissue as it elutes from the drug-eluting balloon.

Figure 1A:
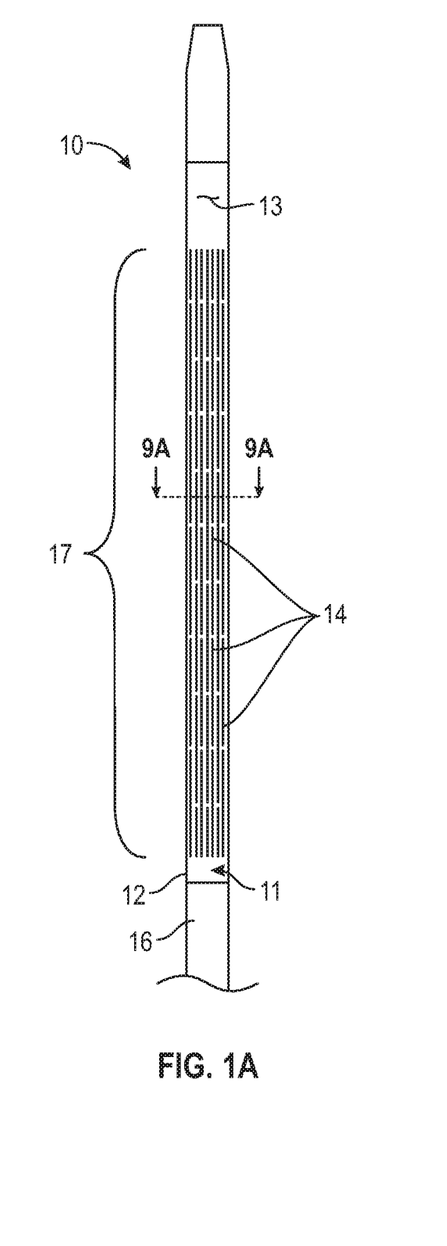
FIG. 1A is a side elevational view of a drug-elution sleeve mounted on a balloon catheter in an unexpanded diametric state in accordance with the present invention.
Figure 1B:
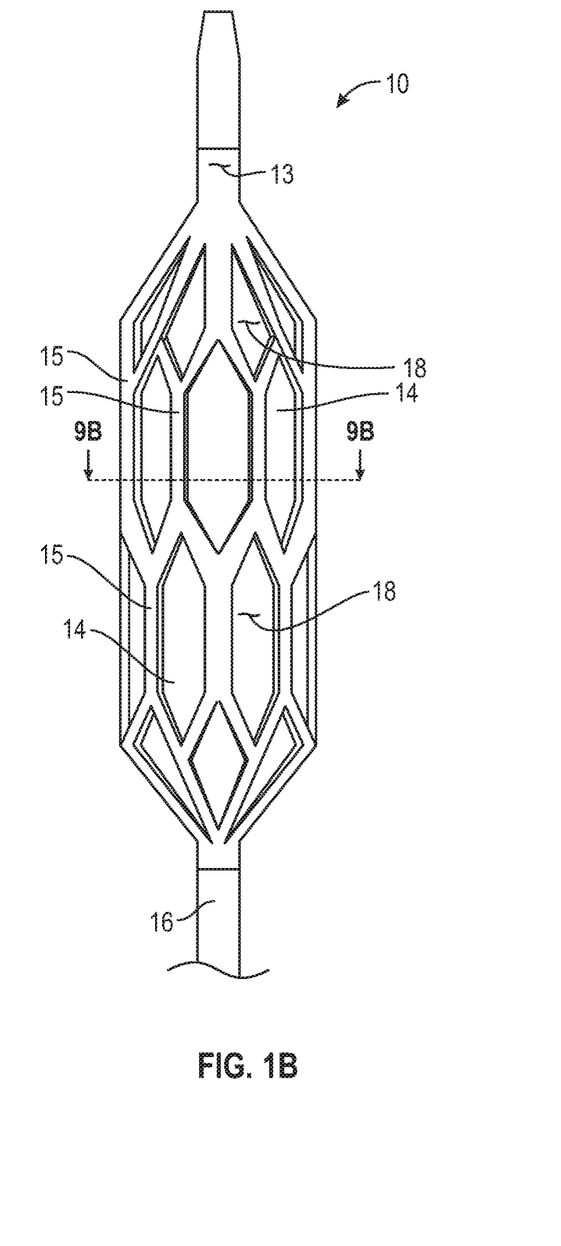
FIG. 1B is a side elevational view of the drug-elution sleeve mounted on a balloon catheter in an expanded diametric state in accordance with the present invention.

Turning now to the accompanying Figures, FIGS. 1A and 1B depict the drug-eluting balloon assembly 10 of the present invention includes a sleeve 12 mounted on an underlying drug-eluting balloon catheter 16. The sleeve 12 has a proximal end 11 and a distal end 13 that are joined to the drug-eluting balloon catheter 16 to couple the sleeve 12 to the drug-eluting balloon catheter 16. FIG. 1A depicts the drug-eluting balloon assembly 10 in its unexpanded diametric state, whereas FIG. 1B depicts the drug-eluting balloon assembly 10 in its expanded diametric state. A plurality of slits 14 are formed in the sleeve 12 and pass through wall surfaces thereof. Each of the plurality of slits 14 are elongate along a longitudinal axis of the sleeve 12 and communicate between a luminal surface of the sleeve 12 and an abluminal surface of the sleeve 12. The plurality of slits 14 are arrayed in a pattern along an intermediate section 17 of the sleeve 12. The intermediate section 17 extends about the circumference of the sleeve 12 and about a substantial extent of the longitudinal axis of the sleeve 12. Proximal end 11 and distal end 13 may be used to couple the sleeve 12 to the drug-eluting balloon catheter 16. The pattern of the plurality of slits 14 is configured to allow for geometric deformation of the plurality of slits 14 as the sleeve 12 is diametrically expanded as the underlying balloon 18 is inflated. During geometric deformation of the sleeve 12, the slits 14 enlarge and open and the land regions 15 deform to expose the drug-eluting balloon 18 beneath the sleeve 12.

Figure 9A:
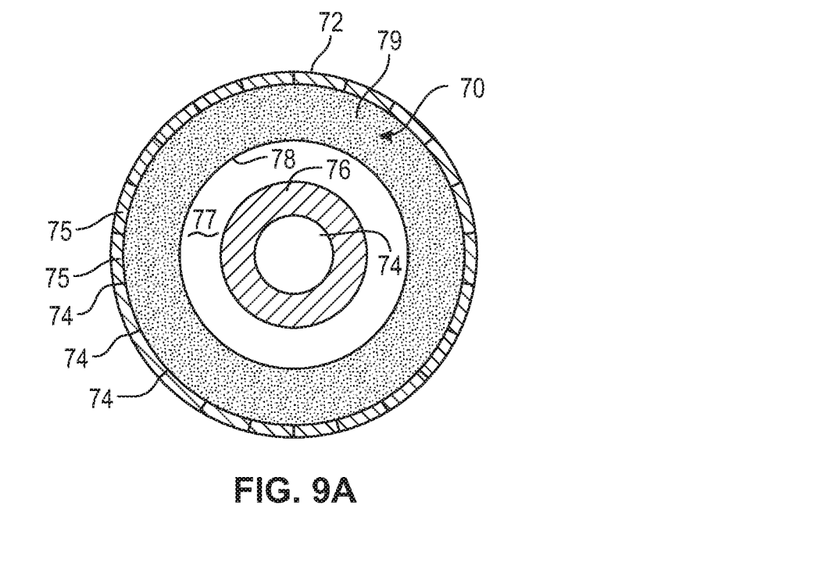
FIG. 9A is a diagrammatic cross-sectional view of a drug-eluting balloon catheter and the drug elution sleeve in diametrically unexpanded state in accordance with the present invention.
Figure 9B:
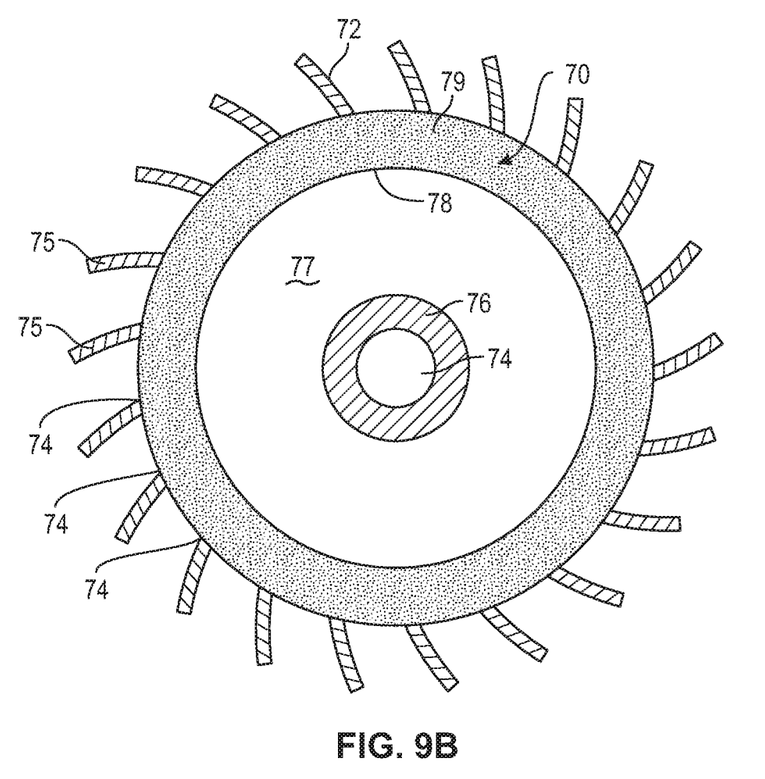
FIG. 9B is a diagrammatic cross-sectional view, taken along line 9B-9B of FIG. 1, of a drug-eluting balloon catheter and drug elution sleeve in a diametrically expanded state.

The generally concentric positional relationship between the sleeve 12, the drug-eluting balloon 18, and the catheter 16 is shown in FIGS. 9A and 9B. FIG. 9A illustrates the assembly in the substantially diametrically unexpanded state, whereas FIG. 9B illustrates the assembly in the substantially diametrically expanded state. In FIGS. 9A and 9B, catheter 76 has a central lumen 74 and carries an inflatable balloon 78 having a drug-eluting or drug coating 79 on an outer surface of the inflatable balloon 78. In its inflated state a fluid filled space 77 is created by introduction of an inflation fluid, not shown, through the lumen 74 of catheter 76. Sleeve 72 is disposed on an outer diametric surface of the drug-eluting or drug coating 79. As previously described, sleeve 72 has a plurality of slits 74 and a plurality of land regions 75. Upon diametric expansion of the balloon, as described above, the slits open under the influence of geometric deformation the sleeve 72, with the land regions assuming a rotated position about their longitudinal axes to project radially outward from the longitudinal axis of the sleeve 72, balloon 78 and catheter 76 to expose the drug-eluting or drug coating 79 to adjacent tissue. Upon release of the expansive force, e.g., due to expansion of balloon 78, the sleeve 72 returns to its unexpanded state with the plurality of land regions 75 returning to a non-rotated state lying substantially normal to the plane of the outer surface of the sleeve 72 as depicted in FIG. 9A.

Both the geometry and arrangement of the plurality of slits 14 may have many different configurations. The plurality of slits will typically be elongate slits. Each of the plurality of slits 14 will have a depth that passes entirely through the wall thickness of the sleeve 12, a length, and a width sufficient to allow the slits to be substantially closed to protect the balloon 18 and drug on the balloon 18 during delivery and open during radial expansion of the sleeve 12 to expose the balloon 18 and the drug coating on the balloon to allow the drug to elute through the open slits 14. Exemplary, non-limiting widths of each of the plurality of slits is between about 0.5 µm and about 10 µm. The width of the plurality of slits 14 may be uniform or variable along the length and circumference of the sleeve 12. The length of each of the plurality of slits 14 may be highly variable and be between about 25 µm to over about 500 µm. Moreover, the length of each of the plurality of slits 14 may be or may not be uniform along the longitudinal and circumferential axes of sleeve 12. For example, a first circumferential row of slits 14 may have a first length, whereas a second circumferential row of slits 14 may have a second length, with the second length is either greater than or less than the first length. The lengths of the slits 14 may be the same or vary along the longitudinal axis of the sleeve 12. Each slit 14 in a given circumferential row of slits 14, however, should have the same length to assure substantially uniform radial expansion of that given circumferential row of slits 14 and the entire sleeve 12. The sleeve 12 of FIGS. 1A and 1B is shown in a flattened plan view in FIG. 2.

Figure 6:
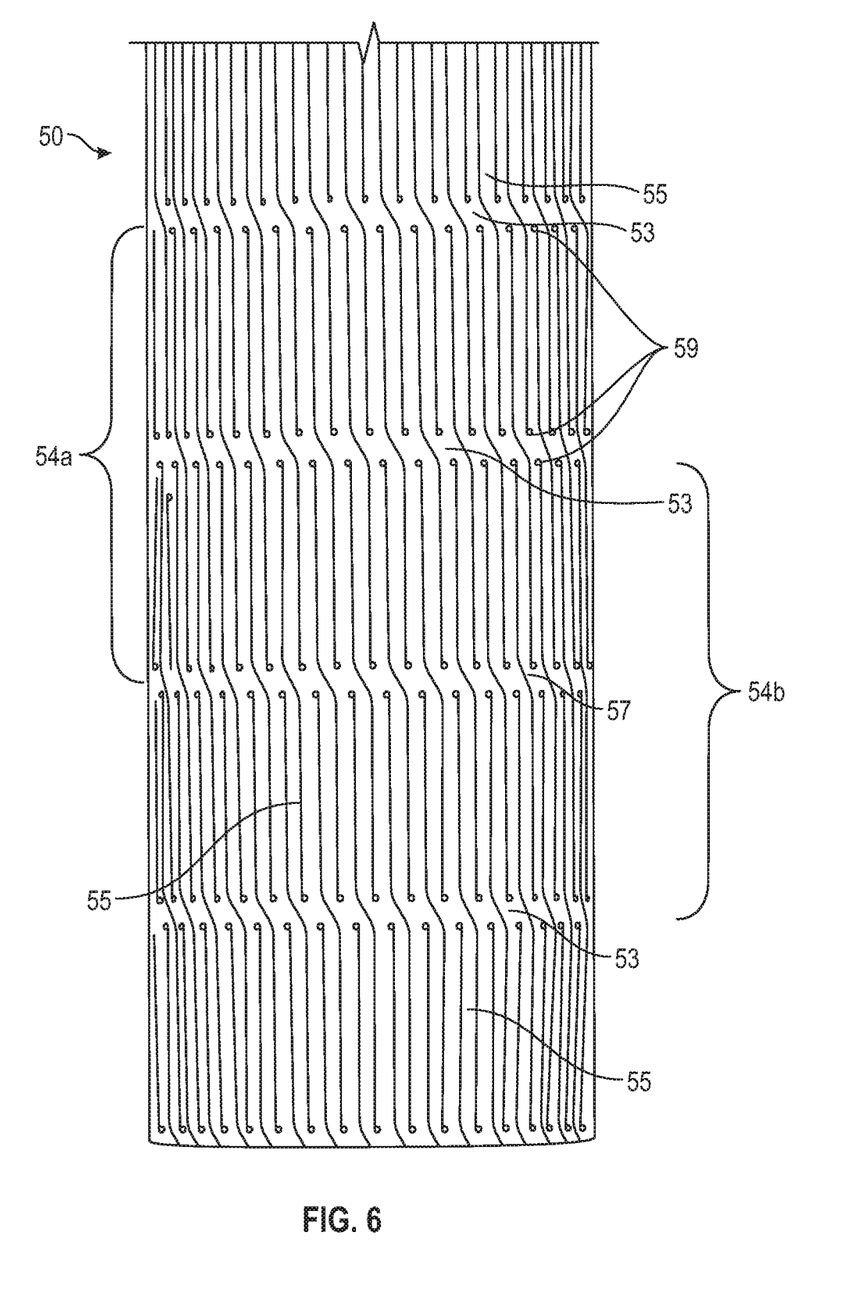
FIG. 6 is a section of an alternative embodiment of the drug-elution sleeve in its unexpanded diametric state in accordance with the present invention.
Figure 7:
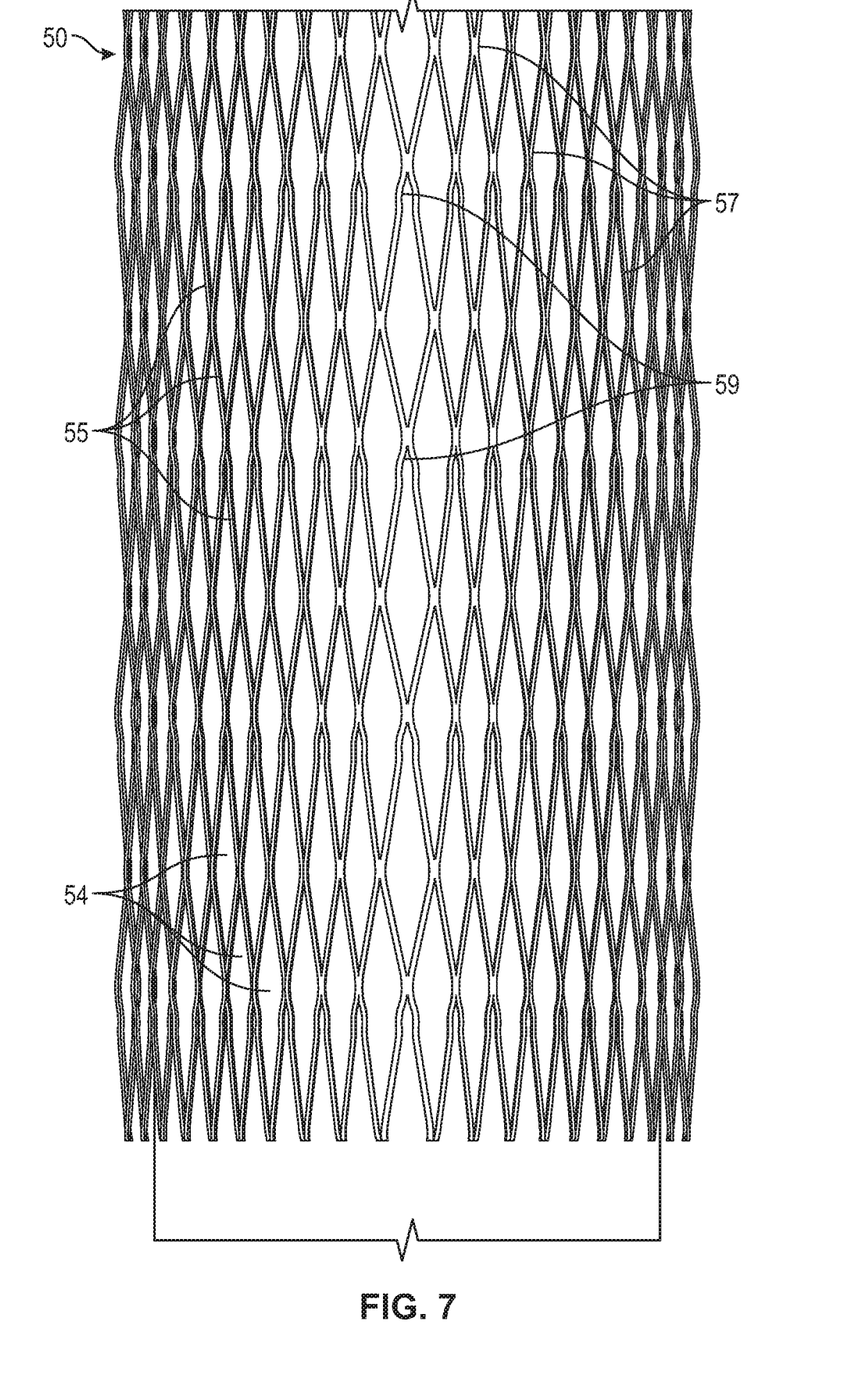
FIG. 7 is a section of the alternative embodiment of the drug elution sleeve shown in FIG. 6 in an expanded diametric state in accordance with the present invention.
Figure 8:
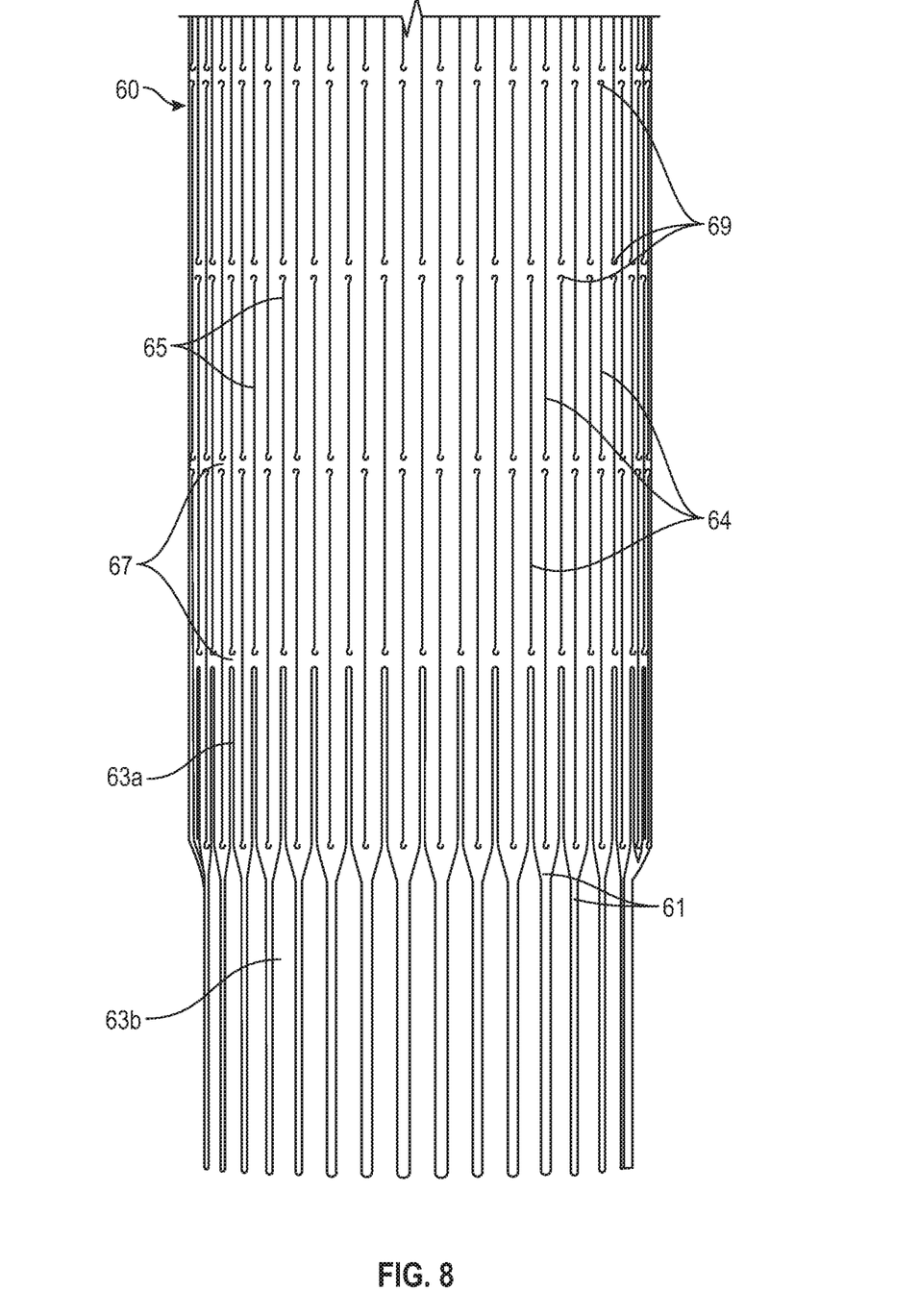
FIG. 8 is a section of another alternative embodiment of the drug-elution sleeve in its unexpanded diametric state in accordance with the present invention.

Further, the plurality of slits 14 may be substantially linear, may have a substantially linear section with an offset section that is oriented helically relative to the circumferential and longitudinal axes of the sleeve 12 or may have a substantially linear section, an intermediate helically oriented offset section and a second substantially linear section as shown in FIG. 6. Optionally, as shown in FIGS. 6-8, at least some and/or all of the plurality of slits may have terminal strain relief sections on either end of the slit 14 or on both ends of each slit 14. The terminal strain relief sections may be configured as a rounded terminal end having substantially the same or greater diameter than the width of the slit 14.

Figure 2:
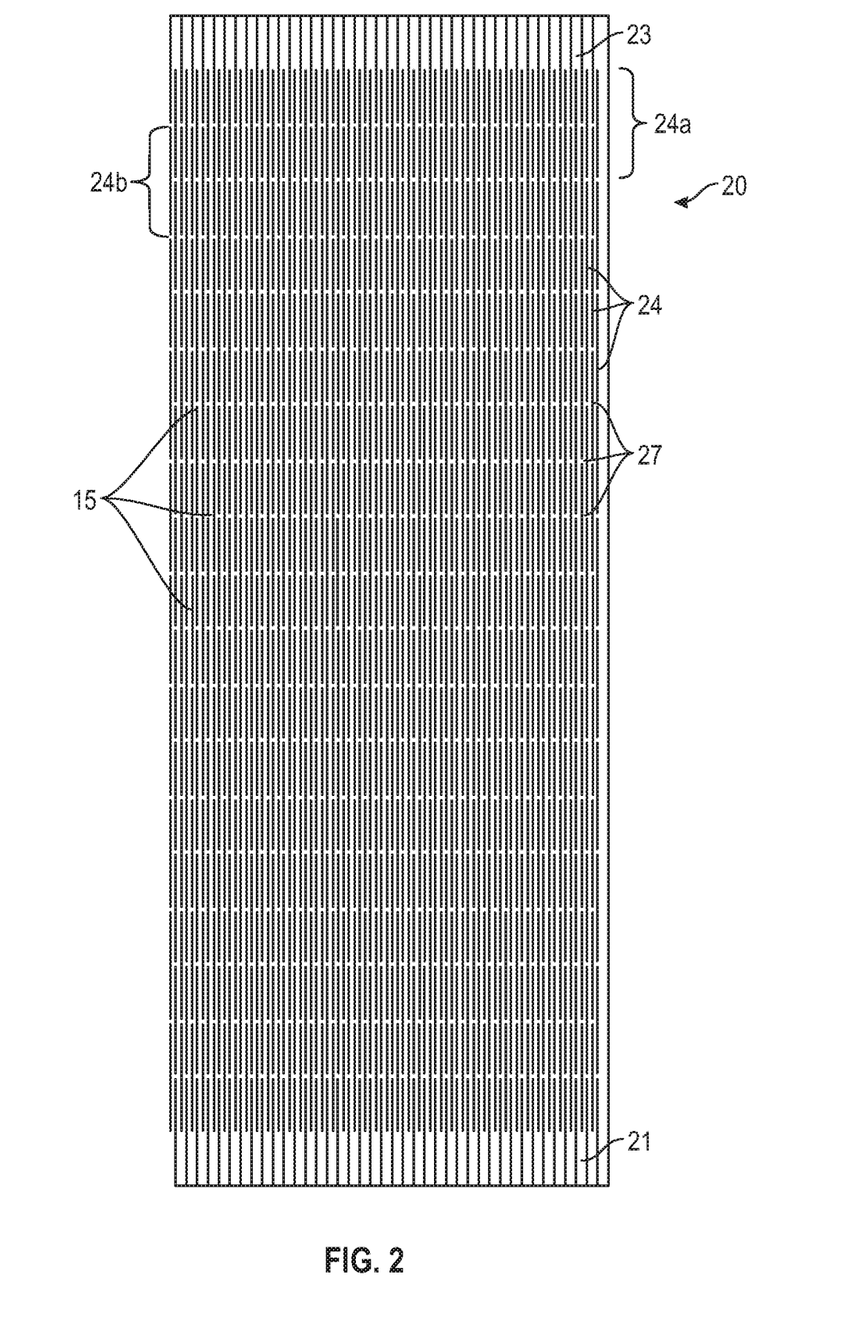
FIG. 2 is a plan view of a slit pattern for the drug-elution sleeve in accordance with the present invention.

With reference to FIG. 2, a plurality of elongate slits 24 are formed in the sleeve 20 and pass through an entire wall thickness of sleeve 20. The plurality of elongate slits 24 patterned in sleeve 20 impart both longitudinal and circumferential compliance to sleeve 20 as well as allow for geometric deformation of the slits during diametric expansion of the sleeve 20 under the influence of balloon expansion. In accordance with one aspect of the invention, the sleeve 20 has a substantially uniform wall thickness between greater than or equal to 0.1µ and less than or equal to 75µ. In this manner, the depth of each of the plurality of elongate slits 24 is also between greater than or equal to 0.1µ and less than or equal to 75 such that each of the plurality of elongate slits 24 is open to a luminal or inner surface of sleeve 20 and an abluminal or outer surface of sleeve 20 along substantially the entire length of each of the plurality of elongate slits 24. When sleeve 20 is in its diametrically unexpanded state, each of the elongate slits 24 have a width less than about 25 µm, preferably less than 15 µm, more preferably less than 10 µm, and most preferably between about 1 µm and 5 µm. Similarly, when sleeve 20 is in its diametrically unexpanded state, each of the plurality of elongate slits 24 preferably have a length greater than about 1 mm. In accordance with an embodiment of the invention, each of the plurality of elongate slits 24 have a width to length aspect ratio greater than or equal to about 1:500 to about 1:120.

Between circumferentially adjacent elongate slits 24 are land areas, synonymously referred to as elongate strut members, 15. Land areas 15 act as the structural scaffold for sleeve 20, forming elongate strut members, and deform in the X-Y plane of the sleeve 20 during radial expansion of the sleeve 20 under the influence of balloon inflation. Additionally, depending upon the configuration of the plurality of slits 24, the land areas 15 may also deform in the Z axis of sleeve 20, such as by at least partially rotating about their individual axes. Hinge regions 27 are present between longitudinally adjacent pairs of the plurality of elongate slits 24 and are positioned at opposing terminal ends of each of the plurality of slits 24. Hinge regions 27 act as hinge points for each of the land areas 15 during radial expansion of the sleeve 20.

Circumferential rows 24a, 24b of slits 24 are arrayed along the longitudinal axis of the sleeve 20. The circumferential rows 24a, 24b may be staggered such that a first set of circumferential rows 24a of slits 24 are longitudinally offset from a second row of circumferential rows 24b of slits 24 each other along the longitudinal axis of the sleeve 20, with a slit 24 of circumferential row 24b being at least partially positioned between adjacent pairs of slits 24 of circumferential row 24a. For example, where all of slits 24 have the same length, a slit 24 in circumferential row 24b may have an end thereof positioned at about one-half the length of the adjacent slits 24 in circumferential row 24a on either side of the slit 24 of circumferential row 24a. In this example, the hinge regions 27 will be positioned with a periodicity along the length of the sleeve 20 which is one-half the length of each slit 24. Thus, if all slits 24 are 100 µm in length, a slit 24 in circumferential row 24b will have opposing ends positioned about 50 µm from ends of adjacent slits 24 in circumferential row 24a. The hinge regions 27, in this case, will also be staggered along the longitudinal axis of the sleeve 20 with a periodicity of about 50 µm or one-half the length of the slits 24.

Sleeve 20 further has a first end 21 and an opposing second end 23. The first end 21 and the second end 23 from proximal and distal ends of the sleeve 20 and serve as attachment points to attach sleeve 20 to either a balloon or to catheter 16. Optionally, terminal rows of elongate slits 24 at the first end 21 and the second end 23 extend to and open to each respective end 21, 23.

Figure 3A:
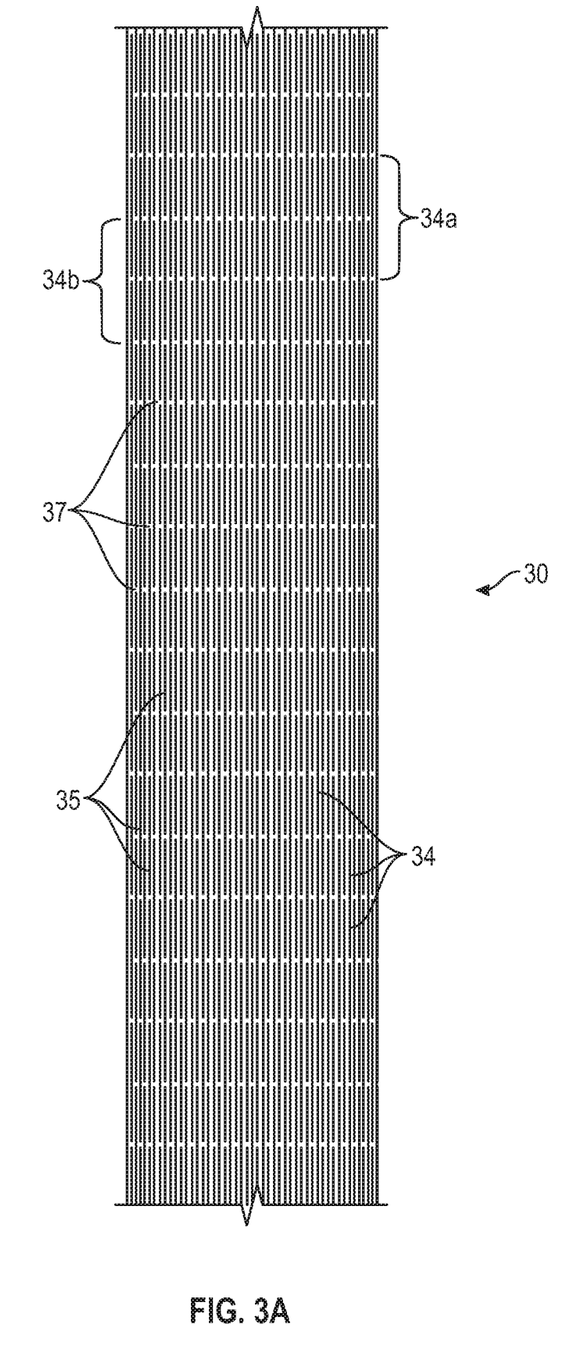
FIG. 3A is a side elevational view of a drug-elution sleeve in its unexpanded diametric state in accordance with the present invention.
Figure 3B:
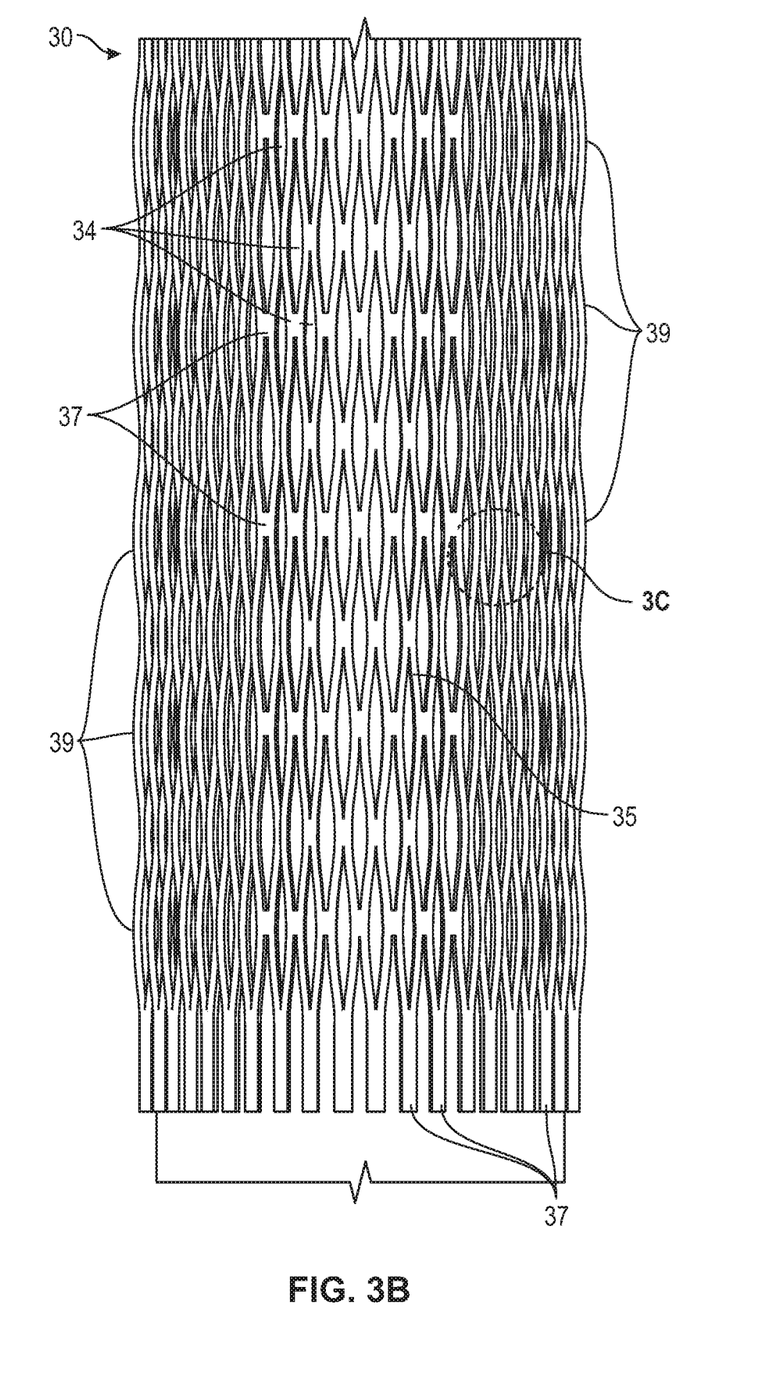
FIG. 3B is a side elevational view of drug-elution sleeve in an expanded diametric state in accordance with the present invention.

FIG. 3A depicts a side elevational view of an intermediate portion 17 of sleeve 20 configured as a tubular sleeve 30 in its diametrically unexpanded state and FIG. 3B depicts a side elevational view of an end portion of sleeve 20 configured as a tubular sleeve 30 in its diametrically expanded state. Like sleeve 20, tubular sleeve 30 has a plurality of elongate slits 34, a plurality of land regions 35 and a plurality of hinge regions 37. The plurality of hinge regions 37 are arranged in rows 34a, 34b extending about the circumference of the tubular sleeve 30 and adjacent rows 34a, 34b extending along the longitudinal axis of tubular sleeve 30. The plurality of elongate slits 34 are arranged a staggered configuration and arrayed in a first row 34a of elongate slits 34 and a second row 34b of elongate slits, each of the first row 34a and the second row 34b are staggered relative to each other such that individual elongate slits 34 are interlaced between the adjacent first row 34a and second row 34b about the entire circumferential axis of the tubular sleeve 30 and along the longitudinal axis of the tubular sleeve 30. In this manner, an end of each slit in first row 34a is adjacent intermediate regions of two circumferentially adjacent slits in second row 34b. This interlaced pattern is repeated along the entire intermediate region 38 of tubular sleeve 30. Intermediate region 38 is positioned between opposing ends (not shown) of the tubular sleeve 30.

FIG. 3B depicts an end section of tubular sleeve 30 of FIG. 3A in a diametrically expanded condition where the plurality of slits 34 have opened and at least some of the land areas 35, or elongate strut members, at least partially rotate about their longitudinal axes and assume an undulating or sinusoidal shape 39 projecting above the normal plane of the outer wall surface of the tubular sleeve 30. The end section of tubular sleeve 30 may, optionally, have terminal projections 37. Terminal projections 37 may simply be extensions of the land areas 35, or elongate strut members, which do not have any of slits 34. Terminal projections 37 may serve as anchors to affix the tubular sleeve 30 to the catheter 16 or to the balloon 18.

Figure 3C:
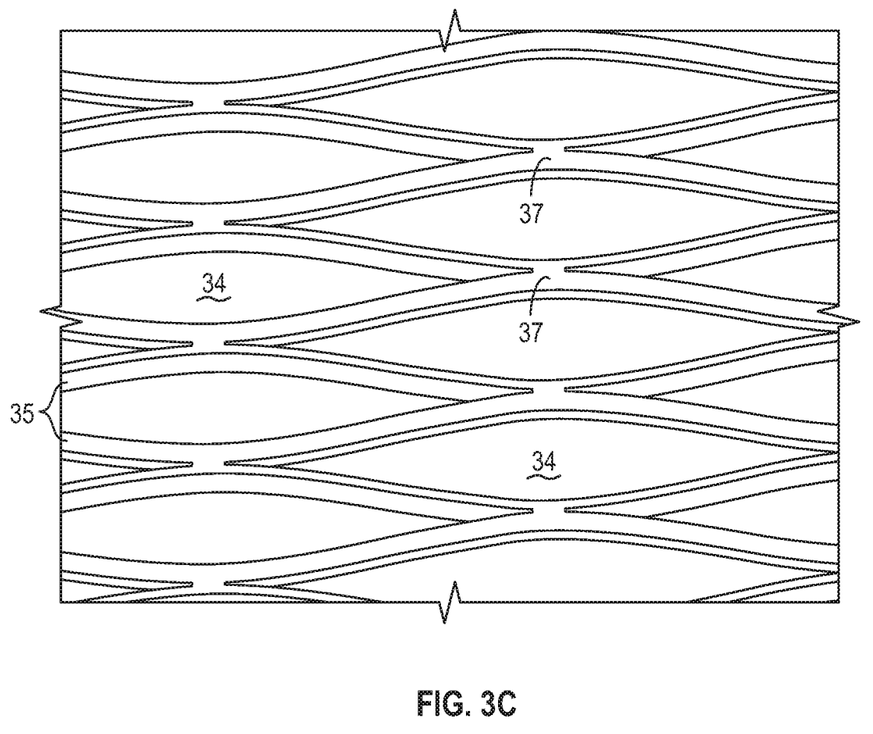
FIG. 3C is an enlarged view of region 3C of FIG. 3B.

FIG. 3C is an enlarged view of a section of tubular sleeve 30 in a diametrically expanded condition. The plurality of slits 34 are opened and the land areas 35, or elongate strut members, are at least partially rotated about their longitudinal axes. Each of the plurality of slits 34 terminate at a hinge region 37 and opposing ends of each of the plurality of slits 34. Each hinge region 37 functions to allow the land areas 35, or elongate strut members, deform in both the X, Y and Z-axis of the tubular sleeve 30 upon diametric expansion of the tubular sleeve 30 under the influence of inflation of balloon 18.

Figure 4:
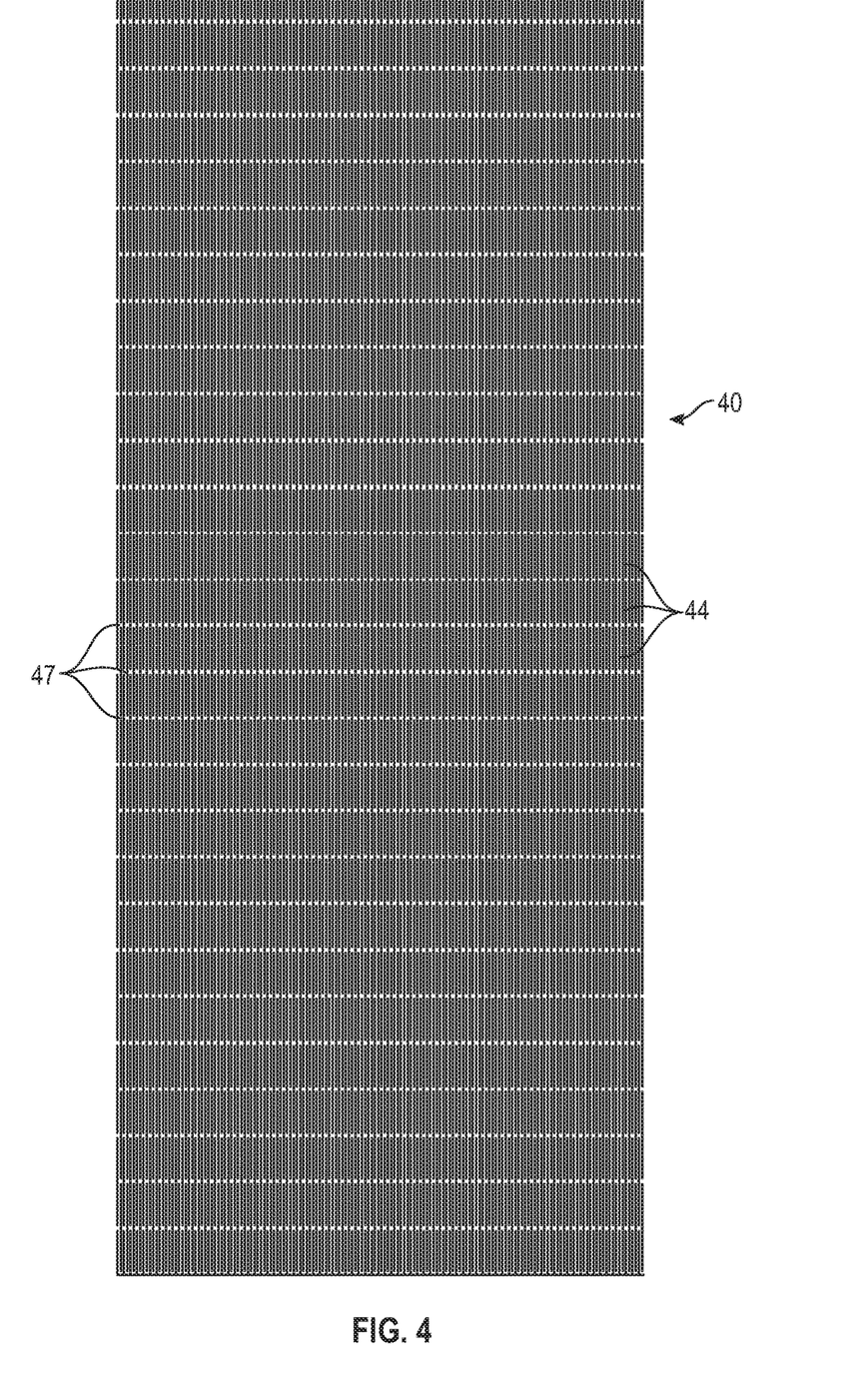
FIG. 4 is a plan view of an alternative slit pattern for the drug-elution sleeve in accordance with the present invention.
Figure 5:
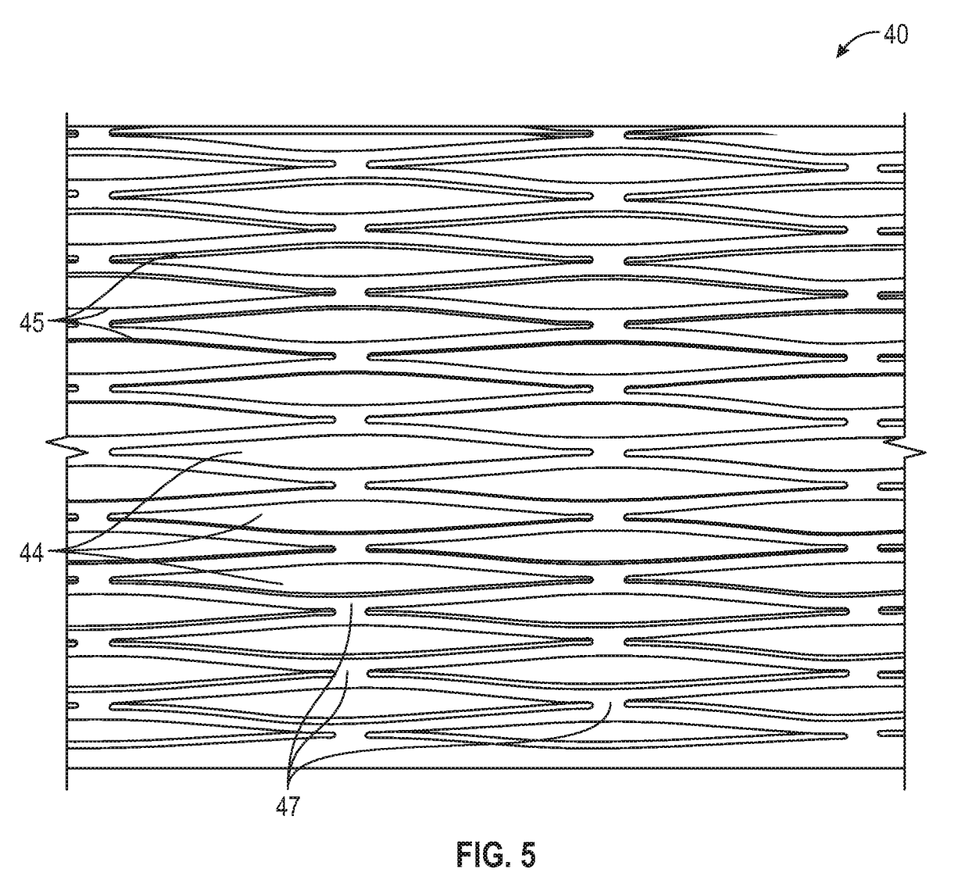
FIG. 5 is an enlarged view of a drug-elution sleeve made in accordance with the slit pattern of FIG. 4.

FIGS. 4 and 5 depict a high density tubular sleeve 40 embodiment in which the plurality of slits 44 have a higher pattern density relative to that in tubular sleeve 30, with a corresponding higher pattern density of the land areas 45, or elongate strut members, and the hinge regions 47. The pattern configuration of the plurality of slits 44 in high density tubular sleeve 40 are generally similar to the configuration of the plurality of slits 34, but have a lower width to length aspect ratio than in tubular sleeve 30. Like tubular sleeves 20, 30, high density tubular sleeve 40 geometrically deforms with the plurality of slits 44 enlarging and opening and land regions 45 geometrically deforming along their length at hinge regions 47 to accommodate opening of the plurality of slits 44. Similarly, the plurality of slits 44 and land regions 45 return to a substantially closed position when an applied force is released, such as by deflation of balloon 18.

Turning to FIG. 6, another alternative embodiment tubular sleeve 50 is depicted. Like tubular sleeve 30 and high density tubular sleeve 40, tubular sleeve 50 has a plurality of elongate slits 54 and a plurality of land areas 55, or elongate strut members, between adjacent pairs of elongate slits 54. The plurality of elongate slits 54 are arrayed in an interlaced pattern such that a first set of elongate slits 54a is circumferentially and longitudinally offset from a second set of elongate slits 54b. At least some of the plurality of elongate slits 54 have an intermediate curved section 53 positioned intermediate between opposing ends of the elongate slits 54. The intermediate curved section 53 extends generally helically relative to the longitudinal and circumferential axes of the tubular sleeve 50. Hinge regions 57 are formed by land areas 55 between longitudinally adjacent pairs of the elongate slits 54. Optionally, strain relief sections 59 may be provided at opposing ends of at least some of the plurality of elongate slits 54. When provided, strain relief sections 59 may be enlarged rounded ends at opposing ends of the elongate slits 54 and act to disburse strain from the land regions 55, or elongate strut members, to the hinge regions 57 during diametric expansion of the tubular sleeve 50. Such enlarged rounded ends of the elongate slits 54 are commonly known as fillets, chamfers or key holes.

FIG. 7 depicts tubular sleeve 50 in a diametrically expanded state in which the plurality of slits 54 are enlarged and open to expose the underlying balloon 18 (not shown). At least some of the plurality of land regions 55 rotate about their longitudinal axes and raise above the normal plane of tubular sleeve 50 to project in a generally sinusoidal, undulating or saw-tooth shape in the Z-axis of the sleeve 50 projecting radially outward from the central longitudinal axis of the catheter 16 (not shown) and the tubular sleeve 50. The intermediate curved section 53 of the plurality of slits 54 helps to facilitate the axial rotation of the land regions 55 about their longitudinal axis and projecting radially outward from the central longitudinal axis of the tubular sleeve 50. Upon removal of a diametrically expansive force, such as deflation of the balloon 18 (not shown) the land regions 55 and plurality of slits 54 return to a substantially closed position and the land regions 55 return to their substantially normal non-projecting state when the tubular sleeve 50 is in its at least substantially non-diametrically expanded state.

Finally, turning to FIG. 8, another alternative embodiment of tubular sleeve 50 is depicted as tubular sleeve 60. Like tubular sleeve 50, tubular sleeve 60 is a substantially tubular member having a plurality of slits 64, defining a plurality of land regions 65 between adjacent slits. At least some of the plurality of slits 64 have terminal strain relief sections 69 at opposing ends of the slits 64. In tubular sleeve 60, however, the plurality of slits 64 are arrayed in circumferential rows that are not circumferentially interlaced. Rather, each of the circumferential rows of the plurality of slits 64 are longitudinally offset from each other along the longitudinal axis of the tubular sleeve 60. At opposing terminal ends of the tubular sleeve 60 are terminal extension members 61 that project proximally and distally from the tubular sleeve 60. For ease of illustration, only one set of terminal extension members 61 are shown in FIG. 8. Terminal slits have a first portion 63a defined between terminal circumferential rows of the land regions 65 and a second portion 63b defined between the terminal extension members 61 projecting from the opposing ends of tubular sleeve 60. While first portion 63a is depicted as narrower in width than second portion 64b, the widths of 63a and 64b may be substantially the same or may be different depending upon device design considerations which are within the skill of one in the art. The terminal extension members 61, like terminal projections 37 in FIG. 3B, may serve as anchors to affix the tubular sleeve 60 to the catheter 16 (not shown) or to the balloon 18 (not shown).

Terminal extension members 61 or terminal projections 37 may be accomplished by any of a wide variety of bonding methods known in the art, including, without limitation, adhesive bonding, thermal bonding, reflowing a compatible material, or the like to join the terminal extension members 61 or the terminal projections 37 to the balloon 18 (not shown) or the catheter 16 (not shown).

In all embodiments of the invention, the sleeve is made a shape memory or superelastic metal, pseudometal or polymer. The sleeve may be fabricated from a planar material rolled into a tubular configuration, which may be coiled or butt-joined, or fabricated from a tubular material, in which case the tubular material is coherent and seamless. Preferably, the sleeve is fabricated from a precursor hypotube which may be made by wrought fabrication techniques or physical vapor deposition fabrication techniques, both of which are known in the art. Physical vapor deposition of shape memory alloys and/or superelastic alloys onto cylindrical mandrels to form coherent, seamless tubes is known in the art. Such processes are exemplified by U.S. Pat. Nos. 6,379,383, 7,335,426, 9,640,359, each of which are hereby incorporated by reference. The plurality of slits in each of the embodiments may be made by various techniques, including, without limitation, machining, such as by laser cutting or electrical discharge machining, lithography, chemical etching, or the like. Where the sleeve is deposited onto a cylindrical mandrel, it is preferable that the plurality of slits be formed in the sleeve while the sleeve is on the cylindrical mandrel, then the mandrel released from the sleeve after forming the slits.

Those skilled in the art will understand and appreciate that the apparatus, system and method of the present invention have been described with reference to exemplary embodiments thereof. Further, while the invention has been described with reference to such exemplary embodiments, variations in dimensions or configuration of the sleeve, slits, land regions, terminal extension members, terminal projections, materials, material properties, or the like are expressly intended and contemplated. The scope of the present invention is intended to be limited only by the claims appended hereto.

The invention claimed is:

1. A balloon catheter, comprising:
   a catheter;
   an inflatable balloon coupled toward a distal end of the catheter;
   a sleeve concentrically positioned about the inflatable balloon and fixed to the catheter, the sleeve comprising shape memory or superelastic material having a plurality of elongate slits passing through the sleeve defining elongate strut members between adjacent pairs of the plurality of elongate slits, the plurality of elongate slits assuming a substantially closed position when the inflatable balloon is in an uninflated state and assuming a substantially open position when the inflatable balloon is in an inflated state, wherein at least some of the elongate strut members are configured to at least partially rotate about their respective longitudinal axes and project radially outward relative to the central axis of the catheter forming an arcuate projection from a normal plane of the sleeve and are additionally configured to return to a substantially co-planar position in the normal plane of the sleeve when the inflatable balloon is in the uninflated state; and
   a drug coating on an outer surface of the inflatable balloon which resides beneath the sleeve when the inflatable balloon is in the uninflated state.

2. The balloon catheter of claim 1, wherein the sleeve is coupled to the catheter at proximal and distal ends of the sleeve.

3. The balloon catheter of claim 1, wherein the plurality of elongate slits further comprises a first set of elongate slits and a second set of elongate slits, the first set of elongate slits and the second set of elongate slits being circumferentially off-set from each other about circumferential and longitudinal axes of the sleeve.

4. The balloon catheter of claim 1, wherein the sleeve has a substantially uniform wall thickness between greater than or equal to 0.1 μm and less than or equal to 75 μm.

5. The balloon catheter of claim 4, wherein each elongate slit of the plurality of elongate slits pass through the wall thickness of the sleeve and have a width less than or equal to 25 μm when the sleeve is in an unexpanded state.

6. The balloon catheter of claim 5, wherein each elongate slit of the plurality of elongate slits has a length greater than 1 mm.

7. The balloon catheter of claim 4, wherein each elongate slit of the plurality of elongate slits has a width to length aspect ratio greater than or equal to 1:500.

8. The balloon catheter of claim 4, wherein each elongate slit of the plurality of elongate slits has a width to length aspect ratio less than or equal to 1:120.

9. The balloon catheter of claim 4, wherein each elongate slit of the plurality of elongate slits have terminal strain relief sections at opposing ends thereof.

10. The balloon catheter of claim 9, wherein each of the terminal strain relief sections further comprises an enlarged rounded section having a diameter greater than a width of a slit within which the terminal strain relief section is associated.

11. The balloon catheter of claim 4, wherein each elongate slit of the plurality of elongate slits further comprises a circumferentially offset section intermediate opposing terminal ends of each slit of the plurality of slits.

12. The balloon catheter of claim 11, wherein at least some of the elongate strut members project radially outward in an undulating manner projecting radially outward and along a central longitudinal axis of the catheter.

13. The balloon catheter of claim 1, wherein the sleeve further comprises proximal and distal couplings configured to couple the sleeve to the balloon catheter.

14. The balloon catheter of claim 1, wherein the sleeve is radiopaque.

15. A sleeve configured to be coupled to a balloon catheter, the sleeve comprising a shape memory or superelastic material having a plurality of elongate slits passing through the sleeve defining elongate land regions between adjacent pairs of elongate slits of the plurality of elongate slits, the elongate slits having a first substantially closed position and a second substantially open position when an expansive force is applied thereto, wherein at least some of the elongate land regions are configured to at least partially rotate about their respective longitudinal axes and project radially outward relative to a central axis of the sleeve when the plurality of slits is in the second substantially open position.

16. The sleeve of claim 15, wherein the plurality of elongate slits further comprises first set of elongate slits and a second set of elongate slits, wherein the first set of elongate slits and the second set of elongate slits are circumferentially off-set from each other about circumferential and longitudinal axes of the sleeve.

17. The sleeve of claim 15, wherein the sleeve has a substantially uniform wall thickness between greater than or equal to 0.1 µm and less than or equal to 75 µm.

18. The sleeve of claim 17, wherein each elongate slit of the plurality of elongate slits pass through the wall thickness of the sleeve and have a width less than or equal to 25 µm when the plurality of elongate slits are in the first substantially closed position.

19. The sleeve of claim 15, wherein each elongate slit of the plurality of elongate slits has a width to length aspect ratio greater than or equal to 1:500.

20. The sleeve of claim 15, wherein at least some of the plurality of elongate slits have terminal strain relief sections at opposing ends thereof.

21. The sleeve of claim 15, wherein at least some of the plurality of elongate slits further comprise a circumferentially offset section intermediate opposing ends of each elongate slit of the plurality of elongate slits.

22. The sleeve of claim 15, further comprising proximal and distal couplings configured to couple the sleeve to the balloon catheter.

23. The sleeve of claim 15 wherein the sleeve is radiopaque.

* * * * *